(12) United States Patent
Guiffant et al.

(10) Patent No.: US 10,799,673 B2
(45) Date of Patent: Oct. 13, 2020

(54) VASCULAR CATHETER PERMITTING THE INJECTION OF A VOLUME OF THE PLUG TYPE

(71) Applicants: Université de Paris, Paris (FR); Centre National de la Recherche Scientifique (CNRS), Paris (FR)

(72) Inventors: Gérard Guiffant, Paris (FR); Jacques Merckx, Paris (FR); Patrice Flaud, Combs-la-Ville (FR)

(73) Assignees: Centre National de la Recherche Scientifique (CNRS) (FR); Université de Paris (FR)

( * ) Notice: Subject to any disclaimer, the term of this patent is extended or adjusted under 35 U.S.C. 154(b) by 0 days.

(21) Appl. No.: 15/576,417

(22) PCT Filed: May 20, 2016

(86) PCT No.: PCT/EP2016/061409
§ 371 (c)(1),
(2) Date: Nov. 22, 2017

(87) PCT Pub. No.: WO2016/188894
PCT Pub. Date: Dec. 1, 2016

(65) Prior Publication Data
US 2018/0147389 A1    May 31, 2018

(30) Foreign Application Priority Data
May 22, 2015   (FR) ...................................... 15 54638

(51) Int. Cl.
*A61M 25/00*     (2006.01)
*A61M 5/00*      (2006.01)

(52) U.S. Cl.
CPC ........... *A61M 25/007* (2013.01); *A61M 5/007* (2013.01); *A61M 25/0023* (2013.01); *A61M 2025/0073* (2013.01)

(58) Field of Classification Search
CPC ........ A61M 25/007; A61M 2025/0073; A61M 25/008; A61M 1/3659; A61M 5/007;
(Continued)

(56) References Cited

U.S. PATENT DOCUMENTS 5,098,413 A   3/1992  Trudell et al.
5,536,261 A   7/1996  Stevens
(Continued)

FOREIGN PATENT DOCUMENTS

WO         9721455 A1    6/1997
WO         0151116 A2    1/2001
WO       2011091275 A1   7/2011

OTHER PUBLICATIONS

International Search Report for PCT/EP2016/061409 dated Dec. 1, 2016.

*Primary Examiner* — Lauren P Farrar
*Assistant Examiner* — Laura C Schell
(74) *Attorney, Agent, or Firm* — Lerner, David, Littenberg, Krumholz & Mentlik, LLP

(57) ABSTRACT

The present invention relates to a single-lumen vascular catheter to be inserted into a blood flow channel for the injection of a product by the venous or arterial route, comprising a tube having a hollow longitudinal body with a lumen, the lumen extending along the full length of the tube and being intended to permit the injection of a given volume of product at a prescribed flow rate the tube having lateral orifices which are of substantially identical size and are arranged in the longitudinal body substantially symmetrically about the longitudinal axis, near a distal end of the
(Continued)

tube, an end surface at the distal end of the tube reducing a total surface area of the lumen starting from the distal end of the tube.

16 Claims, 8 Drawing Sheets

(58) Field of Classification Search
CPC ........ A61M 31/005; A61M 2039/0009; A61M 25/0074; A61M 2025/0079
See application file for complete search history.

(56) References Cited

U.S. PATENT DOCUMENTS

| | | | | |
|---|---|---|---|---|
| 6,117,125 | A * | 9/2000 | Rothbarth | A61M 25/007 604/264 |
| 6,280,434 | B1 * | 8/2001 | Kinoshita | A61M 25/0041 600/435 |
| 6,669,679 | B1 * | 12/2003 | Savage | A61M 25/007 604/131 |
| 2007/0073271 | A1 * | 3/2007 | Brucker | A61M 25/0041 604/537 |
| 2011/0046600 | A1 | 2/2011 | Crank | |
| 2011/0224625 | A1 | 9/2011 | Flickinger et al. | |
| 2013/0053826 | A1 | 2/2013 | Shevgoor | |
| 2014/0018833 | A1 * | 1/2014 | Zhou | A61M 25/0067 606/159 |

* cited by examiner

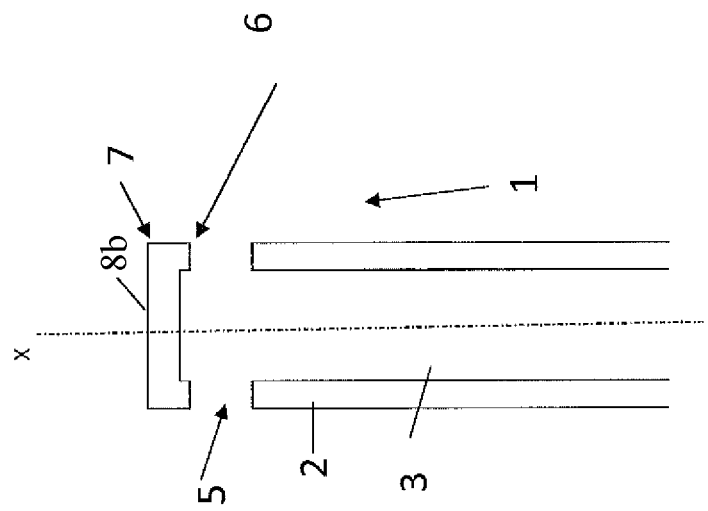
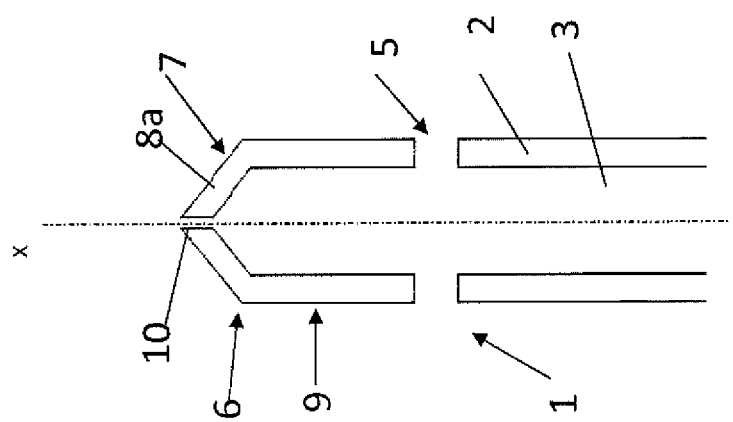

VASCULAR CATHETER PERMITTING THE INJECTION OF A VOLUME OF THE PLUG TYPE

CROSS REFERENCE TO RELATED APPLICATIONS

The present application is a national phase entry under 35 U.S.C. § 371 of International Application No. PCT/EP2016/061409 filed May 20, 2016, which claims priority from European Patent Application No. 1554638 filed May 22, 2015, the disclosures of which are incorporated herein by reference.

FIELD OF THE INVENTION

The present invention relates to the field of vascular catheters permitting the injection of a volume of plug type either for current injection of for vascular opacification. The injected volume is frequently called "bolus" by medical teams and these catheters are often associated with high pressures.

STATE OF THE ART

The parenteral and more particularly intravascular injection of biological, pharmacological or chemical products is current practice.

Of these practices, examination by contrast products is a medical imaging technique which in principle enables viewing of an anatomical structure (hollow organ or vascular arborescence). Injection of the contrast product is generally done by venous or arterial route via a vascular catheter. Irrespective of the type, for the most part vascular catheters are "open termination", i.e., their lumen, single or multiple, terminal and staged, opens full channel in the target vessel: artery or vein. The injection is done once at a high rate to favor formation of a bolus.

The product injected at any rate is more or less rapidly diluted in the blood whereof the average flow in axillary terms is 4-5 mL/s and in cava terms 20 mL/s Tunica intima of vein is thus protected from the corrosive effect of cytolytics, antibiotics, various drugs and hyperosmolar products. To obtain a bolus of contrast product, compatible with 'exploitable' vascular or parenchymal opacification, the injection rates used are from 1 to 5 mL/s. This injection produced by reaction, whiplash, having two horizontal and vertical components likely to mobilize the end of the catheter, responsible for lesion of the vascular endothelium and/or inappropriate migration, in arterial or venous vascular territory.

DESCRIPTION OF THE INVENTION

The present invention relates to a single-lumen vascular catheter intended to be inserted into a blood flow vessel for injection of a product by venous or arterial route, comprising a tube having a hollow longitudinal body having a lumen and extending along the longitudinal axis, the lumen extending fully along the tube and being intended to transport and inject a given volume of product, according to a prescribed rate.

In keeping with the invention, the tube has:
side ports for discharge of the volume of substantially identical size and disposed substantially symmetrically relative to the longitudinal axis of the lumen in the longitudinal body, only near and before the distal end of the tube along the direction of the longitudinal axis (X),
from the distal end of the tube along the direction of the longitudinal axis (X), an end surface fully or partially reducing a total surface of the lumen at the distal end of the tube.

Advantageously, the side ports and the end surface are arranged and dimensioned so that the volume exits radially from the catheter mainly via the side ports and encloses the end of the catheter to stabilize the tube and inject the product out of the catheter radially in the flow of the blood flow channel longitudinal to the tube.

The injection product out of the tube is essentially radial relative to the tube at the side ports, the longitudinal component of the injection out of the tube at the side ports being negligible relative to the radial component, for example equal to 10 to 15% of the radial component adapted to the cross-section of the guide.

The invention relates to catheters for injection of contrast products, but also relates to catheters for injection of other products at lower rates than those used for contrast products. For example, it relates to catheters on the one hand allowing injection of products (antibiotics, parenteral nutrition, cytolytics) and on the other hand blood samples and cardiovascular pressure taps.

Also, these days the same catheter can be used to make a first injection of a product then injection of a contrast product and the catheter of the invention enables this.

In other words, the catheter of the invention having a distal side opening can be used for any distal end: straight for a one-off duration (vascular opacification) or frusto-conical for successive injections of different products whereof the contrast product (therapeutic and vascular opacification usage).

It can be installed provisionally or long-term.

The end surface has a form having progressive reduction of the size of the lumen, from the distal end, pierced by a port. A distal external part of the longitudinal body is situated between the side ports and the end surface of the tube, and is enclosed by the volume of product injected out of the catheter.

The invention:
(i) reduces or eliminates the whiplash effect,
(ii) improves the quality of the bolus at the output of the catheter by improving the filling of the vessel.

Eliminating the whiplash effect improves the reliability of examination with elimination of inappropriate migrations of the catheter.

Improving the formation of the bolus improves the examination quality.

The invention enables injection of plug type by eliminating or limiting any recoil effect of the catheter in the arterial or venous vascular space.

Advantageously, the end surface reduces at least 90% of a total surface of the lumen at the distal end of the tube.

Advantageously, the side ports and the end surface are arranged and dimensioned so that at least 90% of the volume exits the catheter via the side ports.

Advantageously, for a lumen of the catheter having a total given surface and a given radius R, the side ports have dimensions, especially a longitudinal dimension such as a radius if they are circular, calculated so that a sum of the individual surfaces of the side ports is at least equal to the total given surface of the lumen.

Advantageously, a longitudinal dimension of the side ports is calculated to be less than the radius R divided by $\sqrt{2}$.

Advantageously, the side ports have a dimension calculated so that, at equal length, the difference between calculated total hydraulic resistance of the catheter, relative to calculated reference total hydraulic resistance of a catheter with open termination intended to open full channel and having at the end a longitudinal output port corresponding to the lumen, is advantageously less than 5% of the reference hydraulic resistance.

Advantageously, the tube comprises two facing side distal ports.

Advantageously, for therapeutic and radiological or cardiac usage, the distal end surface has a convergent frustoconical shape going beyond the end, pierced by a central port.

Advantageously, the length of the external distal part between the side ports and the end of the tube is less than the radius of the catheter.

Advantageously, the side ports are positioned and have dimensions, especially a longitudinal dimension such as a radius if they are circular, calculated so that concentration of the volume of product at the output of the catheter, according to a prescribed rate, tends to homogenize over a radial distance, relative to a central longitudinal axis of the catheter and at the output of the end of the catheter, close to a diameter of the blood flow channel.

Advantageously, the side ports are positioned and have dimensions, especially a longitudinal dimension such as radius if they are circular, calculated so that the volume of product at the output of the catheter, according to a prescribed rate, is distributed over a radial distance, with advantageously a concentration which tends to homogenize over this radial distance, relative to a central longitudinal axis of the catheter and at the output of the end of the catheter, at least equal to four times a radius R of the lumen of the tube.

Advantageously, for one-off, radiological or cardiac usage, the distal end surface completely closes the lumen, the volume being injected on exiting the catheter at 100% via the side ports.

Advantageously, the other proximal end of the catheter is capable of being attached to a connectable tip of Luer type.

Advantageously, the side ports are made transversally to the longitudinal body.

Advantageously, by way of illustration and non-limiting, the longitudinal body is cylindrical radius of less than 5 mm.

DESCRIPTION OF THE FIGURES

Other aims, characteristics and advantages will emerge from the following detailed description in reference to the appended drawings by way of non-limiting illustration, in which:

FIGS. 1a and 1b illustrate two possible embodiments of the invention; FIG. 1-a schematically illustrates the end of the catheter comprising two symmetrical side ports and an output port; FIG. 1-b schematically illustrates the end of the catheter comprising two symmetrical side ports;

DETAILED DESCRIPTION OF THE INVENTION

Figure 3:
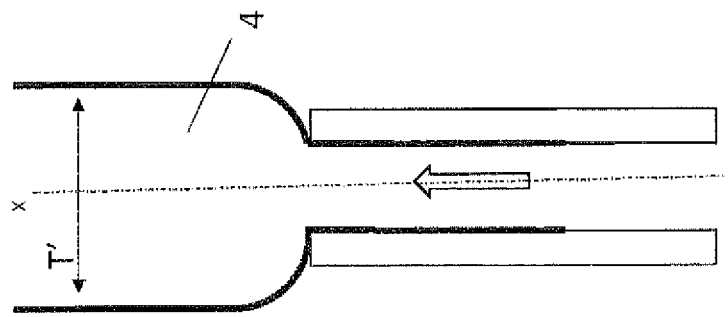
FIG. 3 illustrates a cross-sectional view of a digital simulation of the injection at the output of a catheter of the state of the art comprising a single distal port (with open termination)

The present invention relates to a single-lumen vascular catheter 1 intended to be inserted into a blood flow channel for injection of a product via venous or arterial route, comprising a tube 2 having a hollow longitudinal body along a longitudinal axis X having a lumen 3 (or transversal internal cross-section of the tube 2) here circular extending fully along the tube 2 and intended to receive a given volume 4 of product, according to a prescribed rate.

The tube 2 has side ports 5 which are disposed around the longitudinal axis near each other axially along the longitudinal axis, the side ports 5 being situated along the longitudinal axis X before a distal end 6 and an end surface 7.

The expression 'near' in the paragraph hereinabove means an axial distance between the side ports 5, less than a dimension close to a diameter of the side ports 5, or even advantageously zero or near zero.

Advantageously, the side ports 5 are substantially symmetrical (of a size substantially identical and disposed substantially symmetrically relative to the lumen 3 in the longitudinal body), only near the distal end 6 of the tube 2.

The end surface 7 reduces at least partially the lumen 3 at the distal end 6 of the tube 2.

The end surface 7 is situated after the distal end 6 and the side ports 5 are situated before the distal end 6, relative to the longitudinal direction X oriented from the input of the catheter to the output of the catheter which ejects the product.

The expression 'near' in the paragraph hereinabove means positioning of the side ports 5 relative to the distal end 6 of the tube 2 at distances less than that of a diameter of the tube 2.

The substantially equal and substantially symmetrical side ports 5 and the end surface 7 are arranged and dimensioned so that the volume 4 exits the catheter via the substantially symmetrical side ports 5 and encloses the end of the catheter to stabilize the tube 2 (limiting the whiplash effect) and diffuse the product in the blood flow channel over a large surface radial to the tube 2.

The symmetry of the side ports 5 enables the reaction forces caused by injection at the side ports 5 to be symmetrical (equal and opposite), and avoids deportation of the catheter towards the vessel wall (risk of damage to the endothelium and/or vascular walls), preventing any whiplash effect, and limiting retraction of the catheter.

The catheter limits any displacement during pulsed rinsing.

The adverb 'substantially' for the size of the side ports 5 qualifies the fact that the side ports can be of identical size to 20% (advantageously preferably 10%, and even more advantageously preferably 5%) close to their dimensions, the smallest diameter of a side port being no less than 80% of the largest diameter of another side port (advantageously preferably 90%, and even more advantageously preferably 95%).

The adverb 'substantially' for the positioning of the side ports 5 qualifies the fact that the side ports 5 can have symmetrical positioning relative to the longitudinal axis following the periphery of the tube close to 20% of their dimensions (for example of the largest diameter), advantageously preferably 10%, and even more advantageously preferably 5%.

It is understood that the whiplash effect (longitudinal displacement) and the effect of radial displacement are greatly reduced for side ports rigorously identical in size and which have positioning rigorously symmetrical relative to the longitudinal axis (distribution of side rates via the side ports being identical or almost-identical at this time), and are larger for differences in diameters or positioning of the side ports relative to the longitudinal axis of the order of 15 to 20%.

FIGS. 1-*a* and 1-*b* show the principle of the invention with two different embodiments.

In the first embodiment of FIG. 1*a*, a form projecting over the end, pierced by a central port 10 of minimum diameter enabling only rinsing of the end of the catheter or passage of a guide at the end of the catheter is profiled for the end surface 7.

The central port 10 (also referred to herein as a terminal port, a distal port, and an output port) has a fixed size which is not intended to deform elastically (increase in diameter) during passage of the bolus.

The central port 10 diameter/side port diameter ratio can be for example from 10 to 15%.

The form of the end surface 7 has progressive reduction of the size of the lumen 3.

In this case here, this is a form of a cone 8*a* for the end surface 7 pierced by a small-diameter hole. Two symmetrical side openings or side ports 5 are disposed at the end of the catheter (cf. FIG. 1-*a*, 1-*b*).

These symmetrical side openings allow discharge of the fluid to be injected. Their diameter is provided so as to be closest to the hydraulic resistance which the catheter would have at open end full channel (also called open termination) not provided with this device.

The aim of the terminal port 10 (cf. FIG. 1-*a*) is to permit output flow favoring rinsing of the end of the catheter, without risk of deposits in use at high rate (contrast product) or at low-rate therapeutic injection (antibiotic, cytolytic, parenteral nutrition . . . ).

The terminal port 10 further allows use of a guide (guidewire) favoring positioning of the catheter according to standard technique (Seldinger or other similar techniques).

Also, a distal external longitudinal part 9 of the longitudinal body is situated between the side ports 5 and the end surface 7 of the tube 2, and is enclosed by the volume 4 of product injected out of the catheter.

The length of the distal external longitudinal part 9 between the side ports 5 and the distal end 6 of the tube 2 can be less than the radius R of the catheter, at two or three diameters. It should be noted that the drawings of all the figures and in particular FIGS. 1*a* and 2*a* show the principle of the invention but are not necessarily representative of the scale of the invention.

Advantageously without being limiting, the end surface 7 reduces at least 90%, preferably 95%, the total surface of the lumen 3 at the distal end 6 of the tube 2. The distal end 6 of the tube 2 may further be adapted to the size of the guide used for positioning the tube 2. As demonstrated in FIG. 1*a*, the above-noted reduction in total surface may be according for a shape of the distal end 6 when the guide is not in the terminal port 10.

It can also be possible without being limiting that the side ports 5 and the end surface 7 are arranged and dimensioned so that at least 90%, preferably 95%, of the volume 4 exits the catheter via the side ports 5 according to the size of the tube 2.

In the second embodiment of FIG. 1*b*, the end surface 7 is a straight end 8*b* and the end surface 7 fully closes the lumen 3, the volume 4 being injected at the output of the catheter at 100% via the side ports 5.

It is shown here that the tube 2 comprises two facing side ports 5.

In other embodiments three ports could be made disposed symmetrically relative to the longitudinal axis (at 60° from each other), or 4 ports with two pairs of identical facing ports.

The side ports 5 are advantageously made transversally (or straight relative to the longitudinal surface of the longitudinal body along the axis X) to the longitudinal body and here are substantially circular.

Figure 2B:
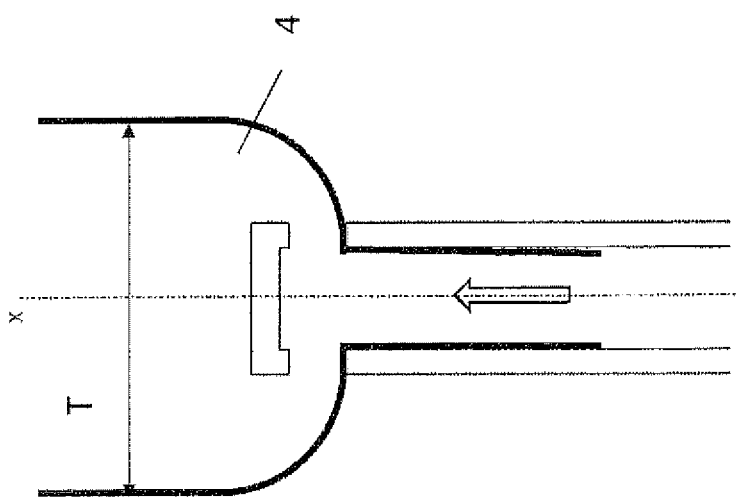
FIGS. 2a and 2b illustrate a cross-sectional view of a digital simulation of the bolus effect (injection of a given volume) at the output of a catheter according to the invention comprising two symmetrical side ports.
Figure 2A:
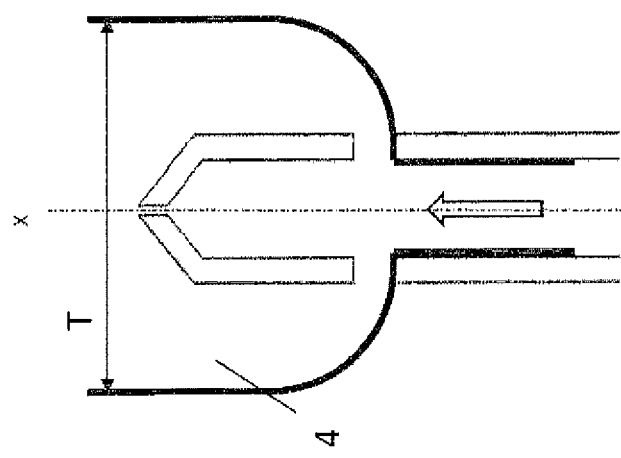

By way of example FIGS. 2*a*, 2*b* and 3 show the formation of the bolus or volume 4 injected with a given concentration at the output of the catheter for the two situations: FIGS. 2*a* and 2*b* in terms of the proposed invention of the catheter with almost-closed or closed termination, FIG. 3 in terms of a classic catheter with open termination.

These drawings come from two simulations presented in the same conditions with an input speed in the catheter: 10 cm/s, input speed in the vein 1 cm/s, diameter of the vein 3 cm, inner diameter of the catheter 2 mm. These simulations show uniform distribution of the concentration in the entire product volume 4 except at the limits of the volume 4 in contact with the blood flow. A very strong gradient is observed at these limits.

Figure 4:
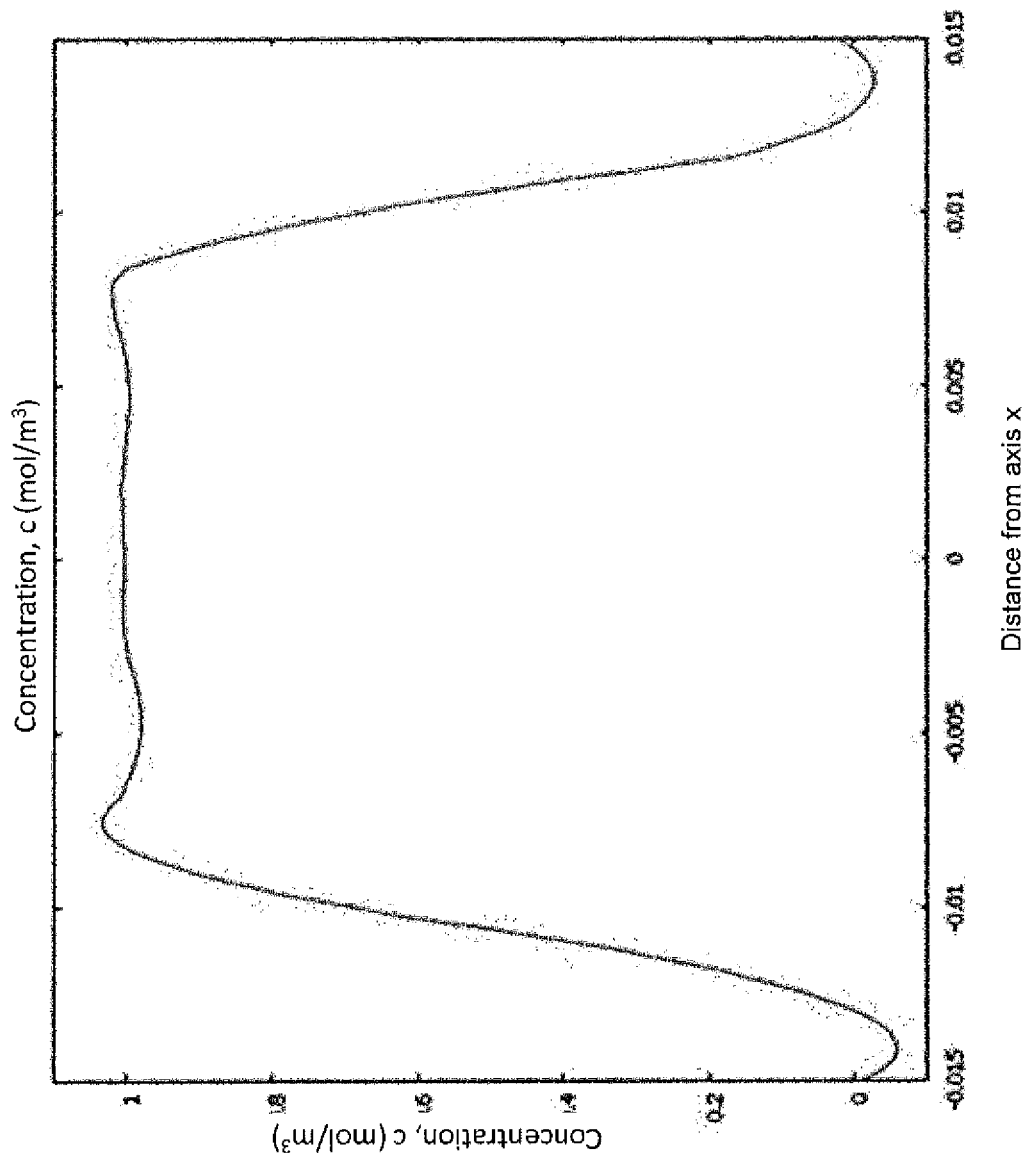
FIG. 4 illustrates a cross-sectional view of the radial distribution of concentration at the output of the catheter in the conditions of FIGS. 2a and 2b, according to a possible embodiment of the invention.
Figure 5:
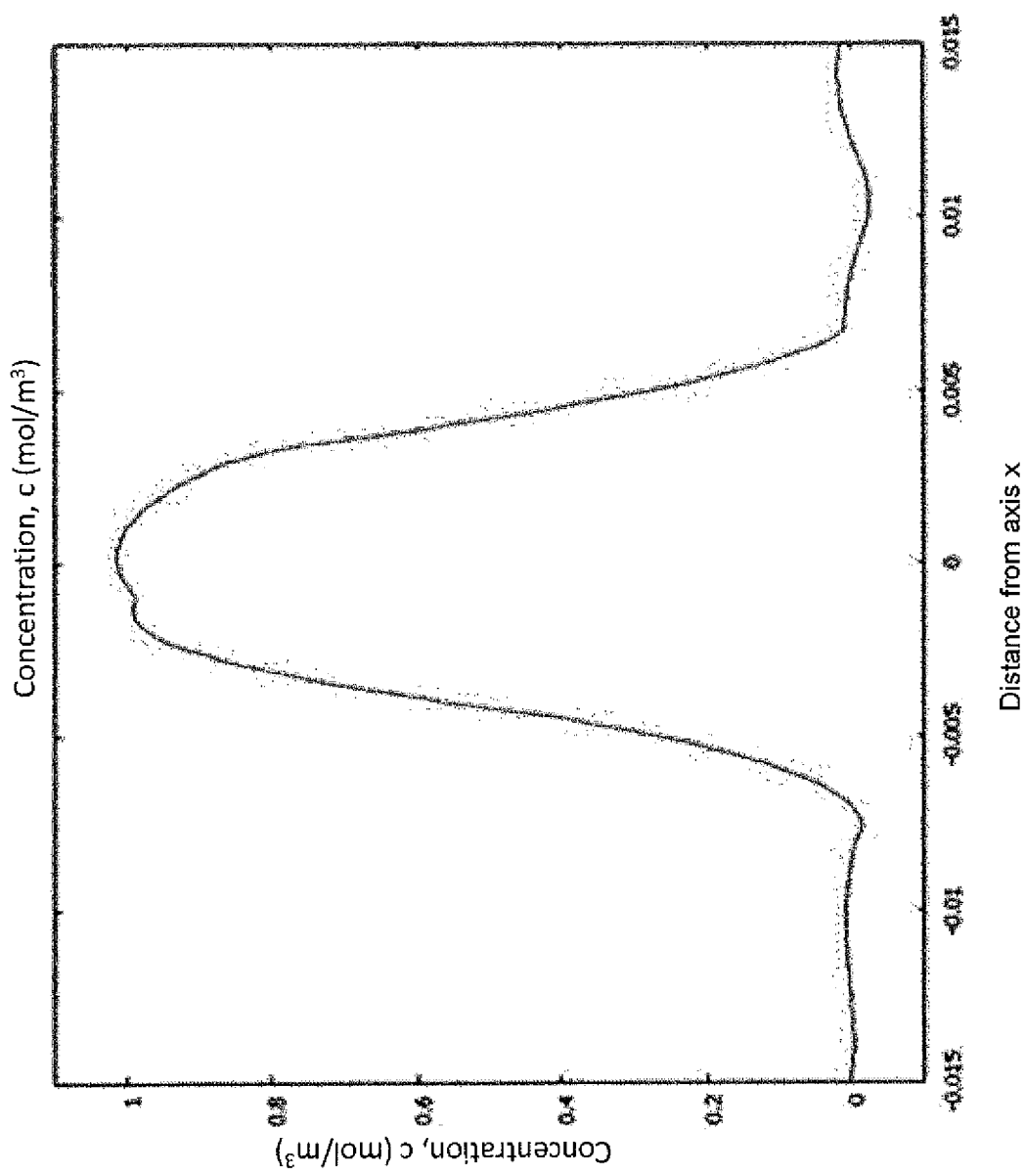
FIG. 5 illustrates a cross-sectional view of the radial distribution of concentration at the output of the catheter in the conditions of FIG. 3, corresponding to a conventional injection.

FIGS. 4 and 5 schematically show distributions of concentration at the output of the catheter in the two cases presented in FIGS. 2*a*, 2*b* and 3. It is very apparent in FIG. 4 that the concentration profile is far more widespread (radial distances T and T') in FIG. 4 corresponding to a side injection.

The radial distance T corresponds, at the output of the catheter (at a longitudinal distance from the end of the catheter equal to a diameter of the blood vessel), substantially to the diameter of the vessel while the radial distance T' at the output of the catheter (at a longitudinal distance from the end of the catheter equal to a diameter of the blood vessel) of the state of the art is only slightly larger than the diameter of the catheter. In other words, T is larger or much larger than T'.

The distance T' will increase in moving away from the catheter in the direction of flow, but the dilution of the product is going to be greater than at the output of the catheter, compared to the invention where suddenly at the output of the catheter, the concentrated bolus of the size of the channel diameter is available. This enables a high image quality of the targeted vessels, the bolus being well distributed radially according to T and few longitudinally along the axis X (compared to the state of the art of FIG. 3 where the bolus is better distributed longitudinally along the axis X than radially along T'). This distance T' depends, for a given ejection time, on the distance travelled by the blood fluid.

This advantage gives less contrast product than in the state of the art of FIG. 3, harmful to health, at least at a quality comparable to what is obtained with the state of the art of FIG. 3. In other words, an equal image quality with less toxicity or a better image quality with equal quantity of contrast product.

Also, and as already described, the catheter according to the invention avoids the whiplash effect and has no blowback effect and/or side mobilization in operation.

The side ports 5 have a dimension longitudinal along the axis X calculated so that the concentration of the volume 4 of product at the output of the catheter tends to be homogeneous over a radial distance T, relative to and perpendicular to a central longitudinal axis X of the catheter and near the end of the catheter, equal to at least four times the radius R.

The hydraulic resistance is the pertinent parameter for characterizing the hydrodynamic performances of a catheter. It should be recalled that the hydraulic resistance is defined, in a flow situation by $$Rh = \frac{\nabla P}{Q},$$

where Q is the rate of perfusion in a conduit of given length with the difference in pressure ∇P applied between the distal and proximal ends of the conduit.

By way of example, different digital simulations have been performed to estimate the impact of symmetrical side ports 5 on the hydraulic resistance of a catheter.

Figure 6:
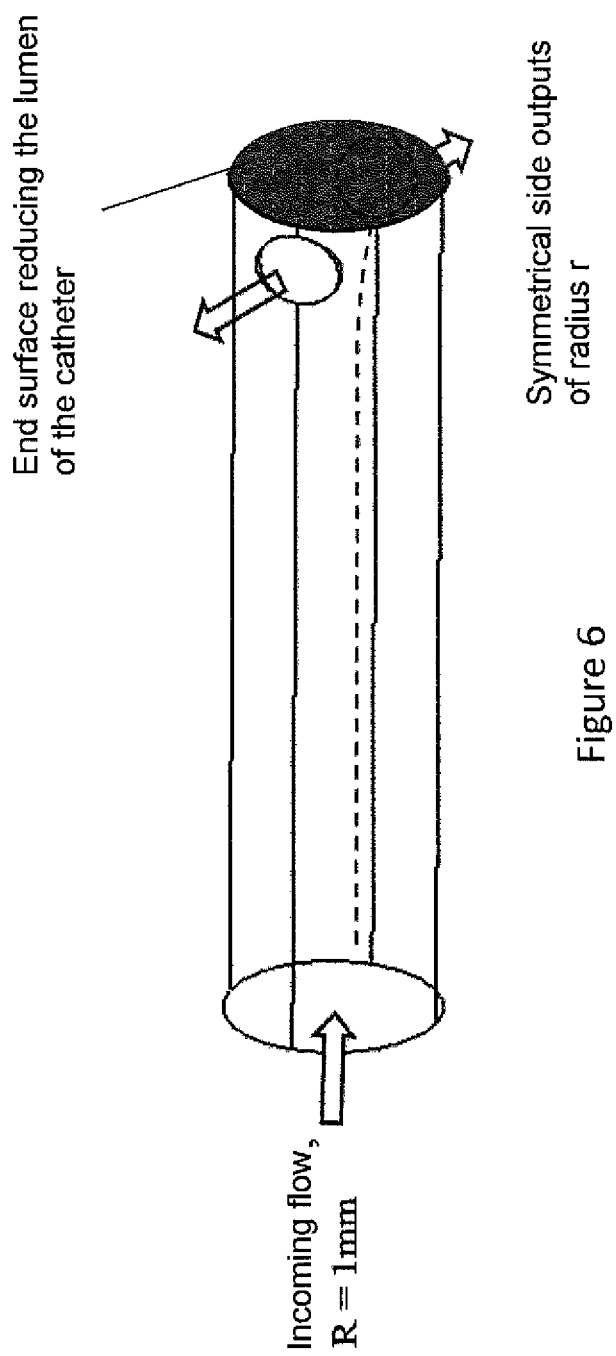
FIG. 6 illustrates the end of the catheter comprising two symmetrical side ports according to an embodiment of the invention.

FIG. 6 shows the notations used: R designates the radius of the catheter and r designates the radius of the symmetrical side openings and corresponds to a longitudinal dimension characteristic of the side openings. A choice was made and the hydraulic resistance will be calculated for different values of r.

Figure 7B:
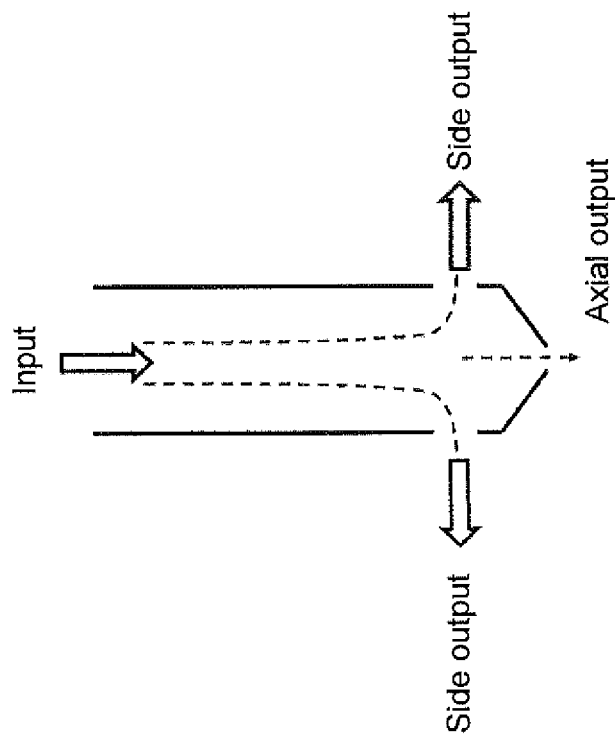
FIG. 7 illustrates the end of the catheter according to the two embodiments of the invention, 7a two symmetrical side ports and a straight end and 7b two symmetrical side ports and a distal port.
Figure 7A:
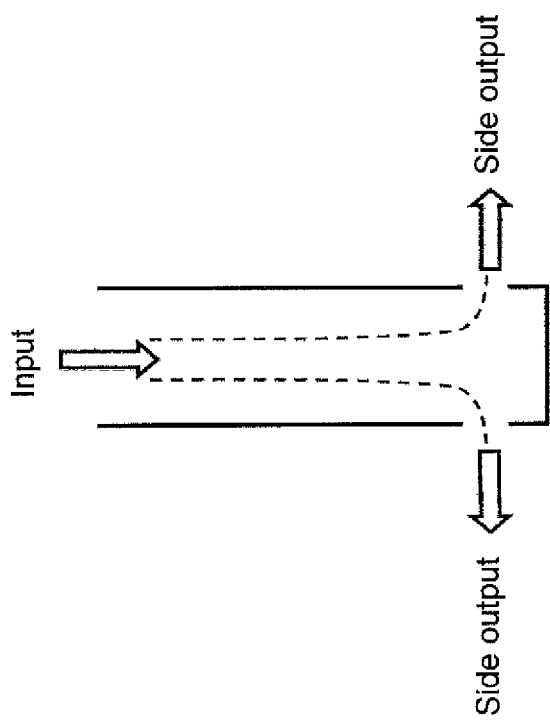

FIGS. 7a and 7b recall the geometry of the end of the catheter and the flow lines depending on whether two symmetrical side openings (FIG. 7a) or two symmetrical side openings are used, completed by a small axial opening for better rinsing (FIG. 7b).

The hydraulic resistance $R_h$ of a segment of the catheter has been calculated for different values of r and this result has been compared to the hydraulic resistance $R_{h0}$ of the same segment comprising a single output distal port (at equal viscosity) called with open termination.

Figure 8:
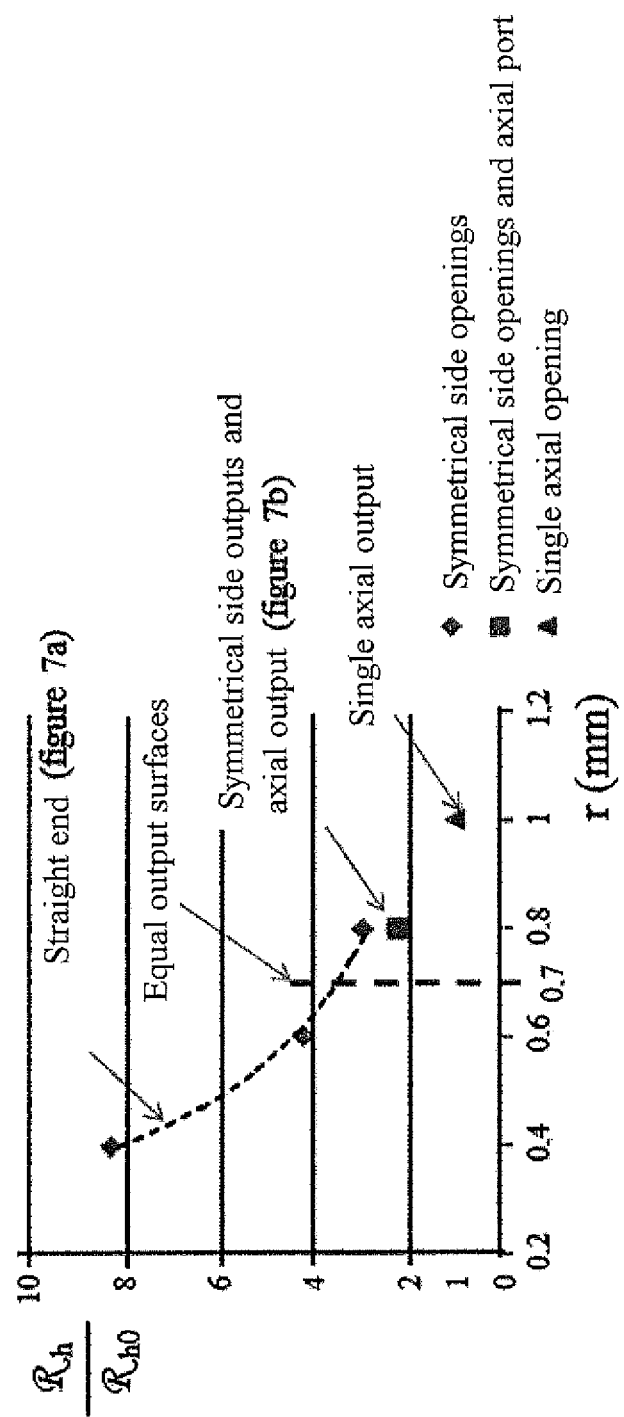
FIG. 8 illustrates the hydraulic resistances (linked to the hydraulic resistance of a conventional end) for the end of a catheter in the different situations presented: single axial opening, symmetrical side openings with or without output port.

FIG. 8 shows the results obtained. It is evident that replacement of an axial distal opening by two symmetrical side openings results in an increase in hydraulic resistance even if the total surface of the symmetrical side openings is identical to the output axial surface (dotted line in FIG. 8). It should be noted that the equality of the surfaces is evidently obtained for $$r = \frac{R}{\sqrt{2}}$$

where R designates the endoluminal radius of the catheter and r the radius of each side port.

This increase in resistance is evidently due to introduction of a curvature of flow lines (cf. dotted lines in FIGS. 7a and 7b).

It is clear that this increase is less if a slight opening is made at the distal end (cf. FIG. 7b). The results are presented by comparing the hydraulic resistances of a catheter open at the end to the hydraulic resistance of a catheter comprising symmetrical side ports 5. This comparison is clearly made for the same fluid injected. In other words, these results depend little on the viscosity of the perfused fluid and are therefore representative of the geometry of the catheter, confirming the interest of the proposed device.

In other words, since the lumen 3 has a total given surface and a given radius R, the side ports 5 can have a longitudinal dimension along the axis X calculated so that the sum of the individual surfaces of the side ports 5 is at least equal to the total given surface of the lumen 3.

The length of the external distal part 9 between the side ports 5 and the distal end 6 of the tube 2 can be selected to be the shortest possible, mechanically supportable for the material of the catheter and the manufacturing method employed.

A distance between a radius and a diameter of the tube 2 should be reasonable to ensure the possibility of satisfactory rinsing and correct mechanical resistance, but this example is not limiting of the invention.

The other end, proximal, of the catheter is capable of being connected to a connectable tip of Luer type.

Catheters can be installed over long periods or provisionally in the human body.

Placement of a vascular catheter 1 satisfies four diverse aims:

intravascular arterial and/or venous pressure tap for evaluating and monitoring cardiovascular hemodynamics.

blood samples for biological analysis purposes continuous or sequential administration of venous or arterial therapeutics isolated and/or iterative administration of contrast products creating vascular opacification (interventional radiology or cardiology).

The vascular catheter 1 prescribed according to the invention is placed for a variable period: brief or prolonged.

To date, each type of aim enacted the placement of a specific catheter type.

Currently, even though controversial at times, the use for one-off examination (vascular exploration) of a venous catheter of long or very long duration is advocated for reducing bodily injury (lesion of the vascular network) and favoring radiological examination (reduction in volume and better concentration of the injected product).

The invention can be implemented and used for any type of catheter:

interventional cardiology or radiology of one-off arterial or venous use, at low or high pressure or rate.

therapeutic administration (Midline, PICCline, PICC Port or High Pressure Catheter with qualified or not implantable room) of long or very long duration, and usable for any injection at lesser rate.

In this sense, the catheter according to the invention is a multi-application catheter which can be used for a large scale of different pressures and different rates (for example by way of illustration only for applications with pressures of the order of 80 to 350 psi and small or extreme rates.

Figure 9:
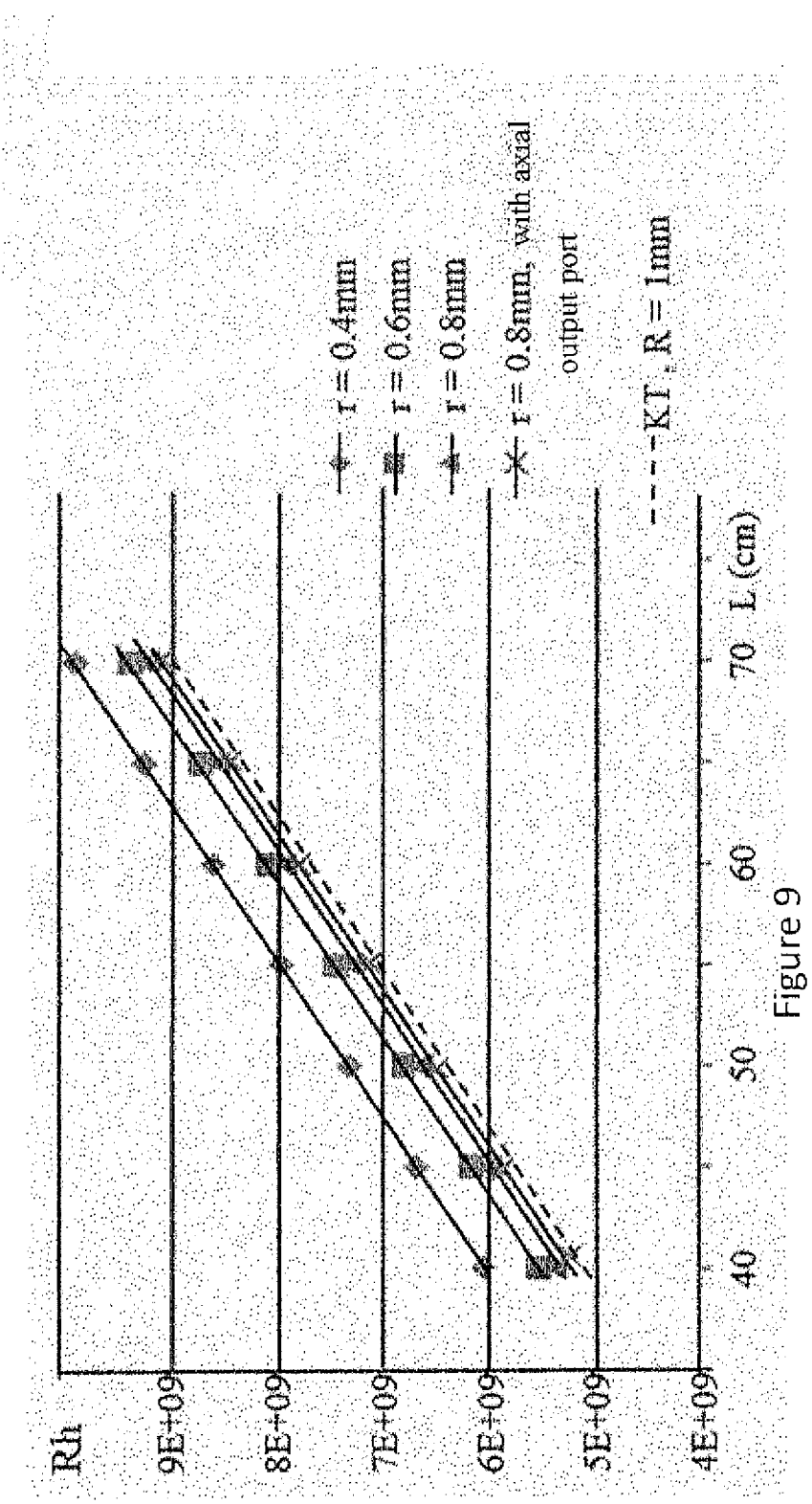
FIG. 9 illustrates the hydraulic resistance of a catheter of internal radius 1 mm as a function of the length, in the different situations presented.

The total hydraulic resistance Rh of a catheter of length L comprising two symmetrical side output ports 5 can now be represented. The results are shown in FIG. 9 for different values of the radius r of the side ports 5 for a catheter length equal to 70 cm.

Dotted lines show the total hydraulic resistance of the catheter comprising a single distal output port only. It is clear therefore that giving the output ports a surface identical to the surface of the lumen 3 of the catheter modifies the total hydraulic resistance of the catheter marginally only (for injection of a product of the same viscosity).

For a catheter of equal length, the variation in total hydraulic resistance does not exceed 3% (for the same viscosity), which is negligible in use for injection of contrast products.

In other words, the side ports 5 have a longitudinal dimension calculated so that, with the catheter at equal length, the difference between calculated total hydraulic resistance of the catheter according to the invention, relative to calculated reference total hydraulic resistance of a catheter with open termination intended to open full channel and having a longitudinal output port corresponding to the lumen 3 at the end, can be less than 5% of the reference total hydraulic resistance.

In summary, in light of the above results it can be estimated that the best choice for the radius r of the symmetrical side openings is situated near the interval:

$$r \approx \frac{R}{\sqrt{2}}$$

The presence of a distal opening of small radius is useful for ensuring better rinsing in particular if the catheter is intended to stay in place (central catheter, PICC Port and PICC line) but also to enable passage of the adapted guideline. The diameter of this distal opening is variable according to the diameter of the catheter and of the leader used (18-22 G).

This distal central opening 10 lets through only a trickle of product for rinsing of the end of the catheter, and it is selected guides of small diameter relative to the side ports of radius r of the tube.

The ratio between the diameter of the side ports and the diameter of the central port 10 is greater than or equal to two, advantageously greater than or equal to four.

A guide of diameter d is first selected, then the central port 10 and the side ports 5 are created in the catheter so that the flow of the product exits essentially via the side ports and negligibly via the central port 10 (less than 10% of volume, advantageously less than 5%).

This proposition relates to all single-lumen vascular catheters of all lengths and all diameters.

For example, they can have a diameter of 3 French to 12 French (0.9 to 4 mm).

For example, they can have any length, lengths greater than 50 cm.

The invention claimed is:

1. A single-lumen arterial or venous vascular catheter for insertion into a blood flow channel for injection of a bolus product in fluid form via venous or arterial route, comprising:
    a tube having a hollow longitudinal body with a longitudinal axis X, a given length, and a lumen, the lumen having a cross-sectional area and a given radius R, wherein the lumen extends fully along the tube and is configured to allow the injection of a given volume of the bolus product, according to a prescribed injection rate of the bolus product in fluid form,
    wherein the tube has symmetrical side ports for discharge of the given volume radially from the tube,
    wherein each of the side ports has an identical size,
    wherein the side ports are disposed symmetrically relative to the longitudinal axis X in the longitudinal body, and wherein the side ports are positioned solely at a position near and before a distal end of the tube along a direction of the longitudinal axis X,
    wherein an end surface of the lumen has a terminal port located at a position after the distal end of the tube along the direction of the longitudinal axis X,
    wherein the end surface of the lumen has a frusto-conical shape that reduces a cross-sectional area of the lumen from the distal end of the tube,
    wherein the terminal port is configured to receive only a guide, and is sized to accept passage of the guide and to enable axial rinsing when the guide is removed,
    wherein the terminal port has a fixed cross-sectional area and is made of a material which is configured to not deform elastically during passage of the bolus product,
    wherein each of the side ports of the catheter has a length along the longitudinal axis X such that, according to the prescribed injection rate of the bolus product in fluid form, a difference between:
        a total hydraulic resistance over the given length of the tube, and
        a reference total hydraulic resistance of a single-lumen reference catheter, wherein the single-lumen reference catheter has only one longitudinal output port for injection fluid, and wherein a length of the single-lumen reference catheter is equal to the given length of the tube, is less than 5% of the reference total hydraulic resistance of the single-lumen reference catheter,
    wherein each side port has a respective cross-sectional area such that a sum of the cross-sectional areas of the side ports is at least equal to the cross-sectional area of the lumen,
    wherein the side ports and the terminal port are dimensioned such that at least 90% of the given volume exits the catheter via the side ports, according to the prescribed injection rate of the bolus product in fluid form when the guide is not in the terminal port, and
    wherein a ratio between a length of either side port along the longitudinal axis X and a width of the terminal port is greater than or equal to two,
    wherein the bolus product in fluid form is a contrast product.

2. The single-lumen vascular catheter according to claim 1, wherein the length of each of the side ports along the longitudinal axis X is such that a concentration of the given volume of the bolus product in fluid form is homogenous over a radial distance T that is at least four times the given radius R, wherein the homogeneity extends in a direction perpendicular to the longitudinal axis X at a distance from the terminal port of the catheter that is equal to a diameter of a blood vessel.

3. The single-lumen vascular catheter according to claim 1, wherein a length of a distal external longitudinal part, situated between the side ports and the distal end of the tube, is less than six times the given radius R of the catheter.

4. The single-lumen vascular catheter according to claim 1, wherein the side ports are perpendicular to the longitudinal axis X of the longitudinal body of the tube.

5. The single-lumen vascular catheter according to claim 1, wherein the side ports are situated at a same longitudinal position along the longitudinal axis X.

6. The single-lumen vascular catheter according to claim 1, wherein the cross-sectional area of a terminating end of the end surface is at least 90% less than the cross-sectional area of the lumen at the distal end.

7. The single-lumen vascular catheter according to claim 1, wherein the ratio between the length of each of the side ports and the width of the terminal port is greater than or equal to four.

8. The single-lumen vascular catheter according to claim 1, wherein the ratio between the length of each of the side ports and the width of the terminal port is between 10 to 15%.

9. The single-lumen vascular catheter according to claim 1, wherein the side ports are dimensioned to produce an injection rate of the bolus product between 0.5 to 5 mL/s, at pressures of the order of 80 to 350 psi.

10. The single-lumen vascular catheter according to claim 1, wherein the side ports are circular and having a radius r, and wherein the length of the side ports is a diameter twice the radius r, such that a sum of the cross-sectional areas of all the side ports is at least equal to the cross-sectional area of the lumen at the distal end, and wherein r is at least equal to:

$$r = \frac{R}{\sqrt{2}}.$$

11. The single-lumen vascular catheter according to claim 1, wherein the side ports comprise two side ports.

12. The single-lumen vascular catheter according to claim 1, wherein the side ports comprise three side ports.

13. The single-lumen vascular catheter according to claim 1, wherein the side ports comprise four side ports with two pairs of identical side ports.

14. The single-lumen vascular catheter according to claim 1, wherein the catheter is chosen among:
 a Midline;
 a PICCline;
 a PICC Port;
 a Catheter; or
 a High Pressure Catheter.

15. The single-lumen vascular catheter according to claim 1, whereby the end surface of the lumen having the frusto-conical shape acts as an axial stopper to a flow of the bolus product.

16. A catheter comprising:
 a tube including a lumen extending from a distal end of the tube to a front tip of the tube along a primary axis, wherein the front tip of the tube is tapered such that a diameter of the lumen at the front tip is less than a diameter of the lumen at the distal end;
 a first port formed on a side of the tube and having a first diameter, the first port being configured to discharge a first portion of the tube's contents in a first direction extending radially from the primary axis;
 a second port formed on the side of the tube and having a second diameter equal to the first diameter, the second port being configured to discharge a second portion of the tube's contents in a second direction extending radially from the primary axis, wherein the second direction is opposite the first direction, and wherein the first and second ports are positioned equidistant from the distal end of the tube;
 a third port having a third diameter and located at the front tip of the tube and configured to discharge a third portion of the tube's contents in a third direction along the primary axis, wherein the third port is made of a rigid material that does not deform during discharge of the third portion of the tube's contents,
 wherein the first, second and third diameters are dimensioned such that, for a bolus injection of a contrast product injected through the catheter in fluid form at an injection rate of between 0.5 to 5 mL/s and a pressure between 80 to 350 psi:
  inclusion of the first and second ports in the catheter changes a total hydraulic resistance of the catheter by less than 5% as compared to the first and second ports being not included in the catheter,
  90% or more of the contrast product is discharged from the catheter through the first and second ports,
  a sum of the cross-sectional areas of the first and second ports is equal or greater than to a cross-sectional area of the lumen at the distal end, and
  a ratio between the first diameter and the third diameter is greater than or equal to two.

* * * * *